(12) United States Patent
Schenk et al.

(10) Patent No.: US 6,287,793 B1
(45) Date of Patent: *Sep. 11, 2001

(54) DIAGNOSTIC METHODS FOR ALZHEIMER'S DISEASE

(75) Inventors: Dale B. Schenk, Redwood City; Robin M. Barbour, Newark; Kelly L. Johnson, Santa Cruz, all of CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/850,142

(22) Filed: Mar. 12, 1992

Related U.S. Application Data

(63) Continuation of application No. 07/235,055, filed on Aug. 19, 1988, now abandoned.

(51) Int. Cl.⁷ ............................ G01N 33/543; C12P 21/08
(52) U.S. Cl. ..................... 435/7.95; 435/70.21; 436/548; 436/811; 530/388.25
(58) Field of Search ................. 530/388.25; 435/7.1, 435/7.95, 23, 70.21; 436/518, 548, 811, 815, 821

(56) References Cited

U.S. PATENT DOCUMENTS

| | | | |
|---|---|---|---|
| 4,097,586 | 6/1978 | Gross | 424/1 |
| 4,123,427 | 10/1978 | Daniel | 530/389.5 |
| 4,185,084 | 1/1980 | Mochida et al. | 424/1 |
| 4,264,766 | 4/1981 | Fischer | 536/51 |
| 4,294,818 | 10/1981 | McMichael et al. | 424/12 |
| 4,298,592 | 11/1981 | Lin et al. | 424/1 |
| 4,378,428 | 3/1983 | Farina et al. | 435/7.23 |
| 4,471,052 | 9/1984 | Smith et al. | 436/518 |
| 4,474,892 | 10/1984 | Murad et al. | 436/513 |
| 4,496,658 | 1/1985 | Kondo et al. | 436/510 |
| 4,508,830 | 4/1985 | Baker et al. | 436/510 |
| 4,595,661 | 6/1986 | Cragle et al. | 436/534 |
| 4,623,621 | 11/1986 | Pestka | 435/7.94 |
| 4,642,284 | * 2/1987 | Cooper et al. | 435/7 |
| 4,649,106 | 3/1987 | Schlossman et al. | 435/7.24 |
| 4,659,678 | 4/1987 | Forrest et al. | 436/512 |
| 4,661,446 | 4/1987 | Schlossman et al. | 435/7.24 |
| 4,666,829 | 5/1987 | Glenner et al. | 435/6 |
| 4,670,383 | 6/1987 | Baier et al. | 435/7.92 |
| 4,675,386 | 6/1987 | Royston et al. | 530/387 |
| 4,707,438 | 11/1987 | Keydar | 435/5 |
| 4,722,889 | 2/1988 | Lee et al. | 435/7.94 |
| 4,782,014 | * 11/1988 | Serban et al. | 435/7 |
| 4,801,533 | * 1/1989 | Fudenberg | 435/7.24 |
| 4,902,630 | * 2/1990 | Bennett et al. | 436/546 |
| 4,946,774 | * 8/1990 | Oh | 435/7 |

FOREIGN PATENT DOCUMENTS 0249007   4/1987   (EP) .

OTHER PUBLICATIONS

Galfre & Milstein—*Methods in Enzymology* vol. 73:3–45 ('81).
Giometto et al., Eur. Neurol. (Switzerland) 28(1): 30–33, 1988.*
Behan et al., Chem. Abs. 73(19): 96527h.*
Sevier et al., Clin. Chem. 27(11): 1797–1806, 1981.*
Sigma Chemical Co. Catalog, pp. 709–712, 1987.*
Cytotech Product Catalog, Cat. #1018, #1024, 1988.*
Thal et al., J. Amer. Geriat. Soc 35:1047–1050, 1987.*
Henry, J.B., *Clinical Diagnosis and Management by Laboratory Methods*, 17th Edition, W.B. Saunders Co., Philadelphia (1984), p. 213.*

* cited by examiner

Primary Examiner—Donna C. Wortman
(74) Attorney, Agent, or Firm—Lisabeth F. Murphy

(57) ABSTRACT

Methods are disclosed for the identification of key diagnostic antibodies and antigens characteristic of a disease state of interest. Key diagnostic antibodies and antigens, diagnostic kits, and methods for diagnosis, are disclosed for Alzheimer's disease.

29 Claims, 5 Drawing Sheets

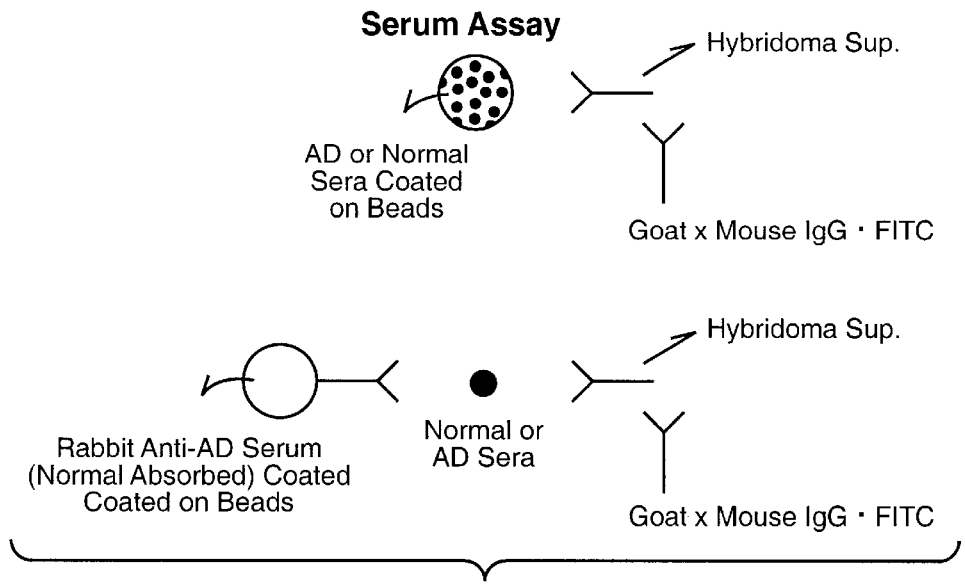
FIG._1
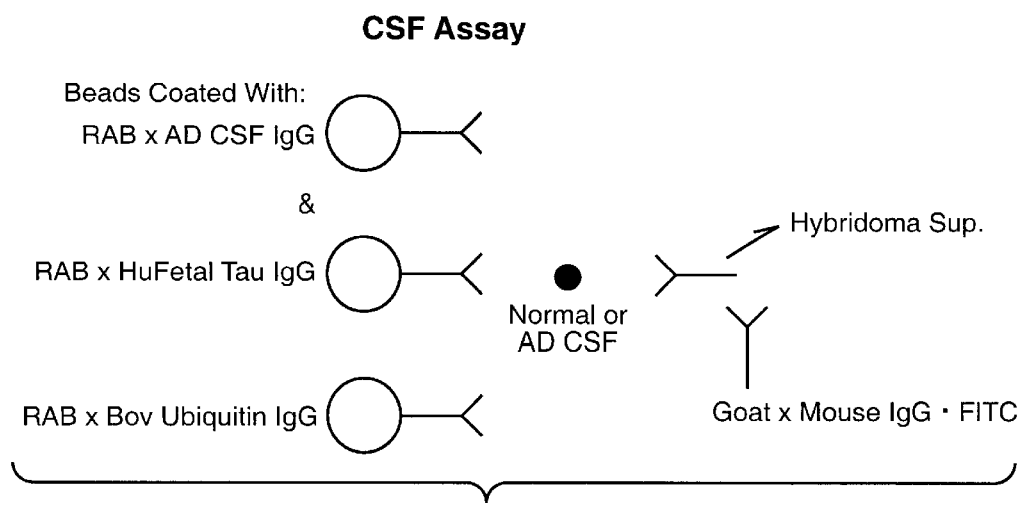
FIG._2

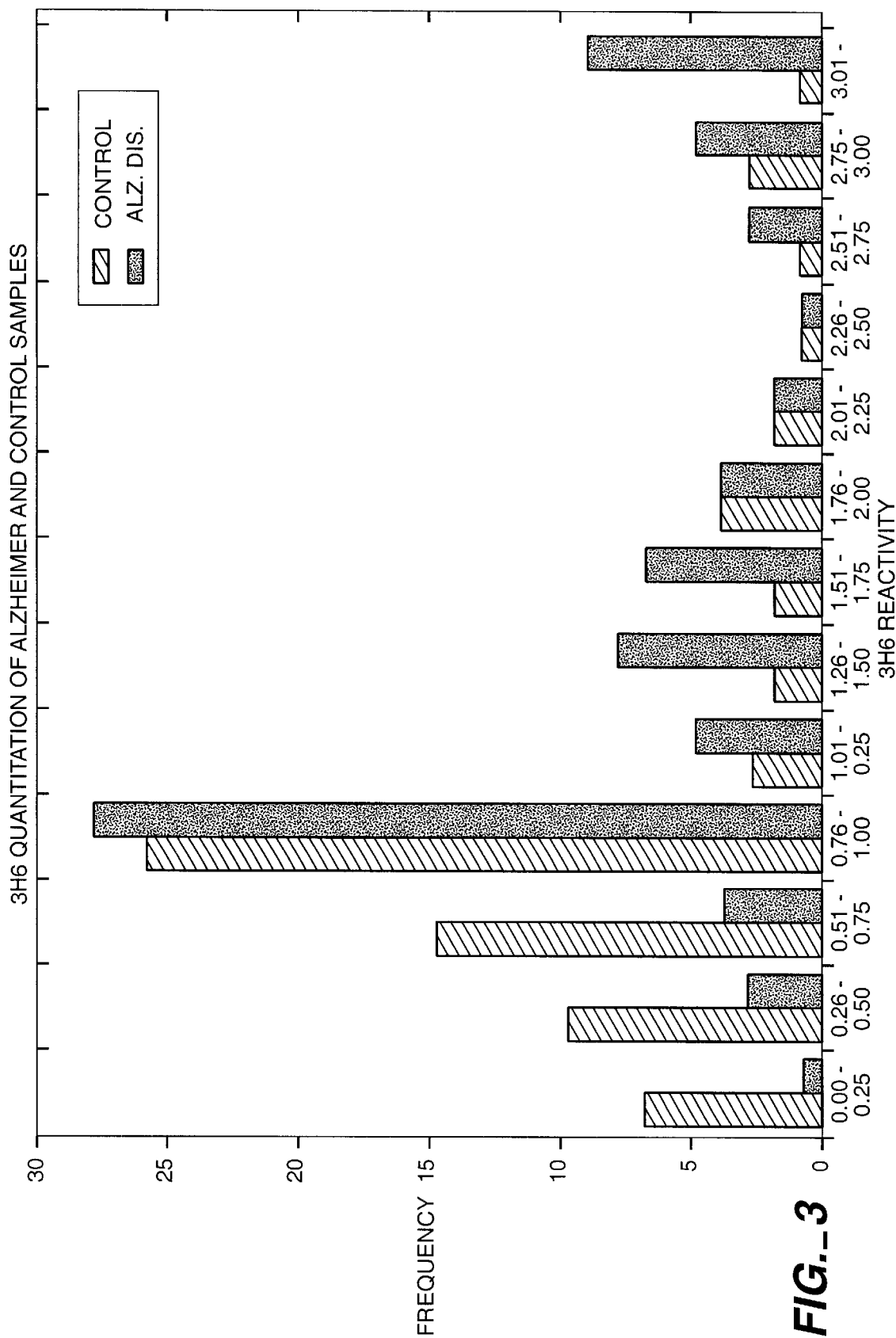
FIG._3

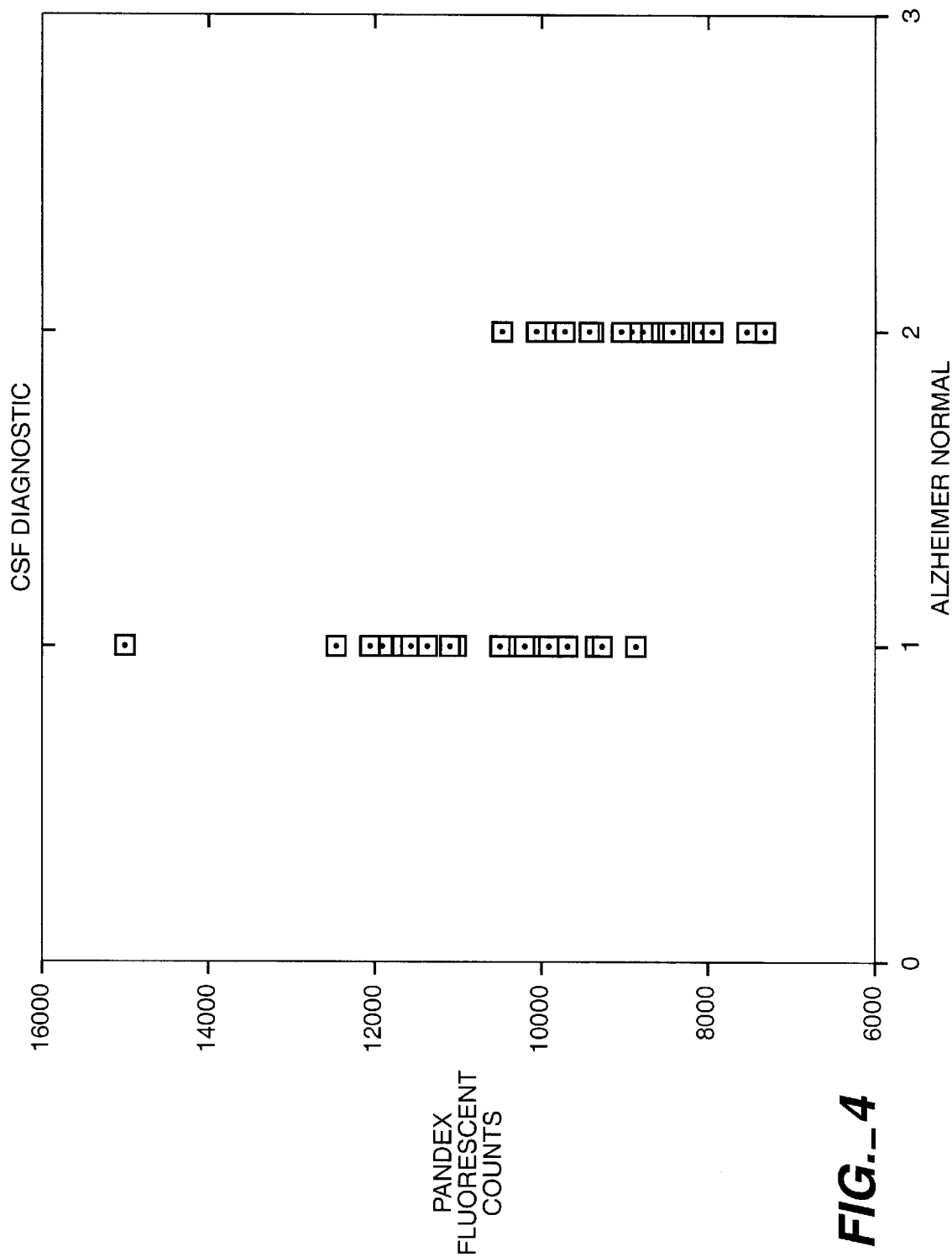
FIG._4

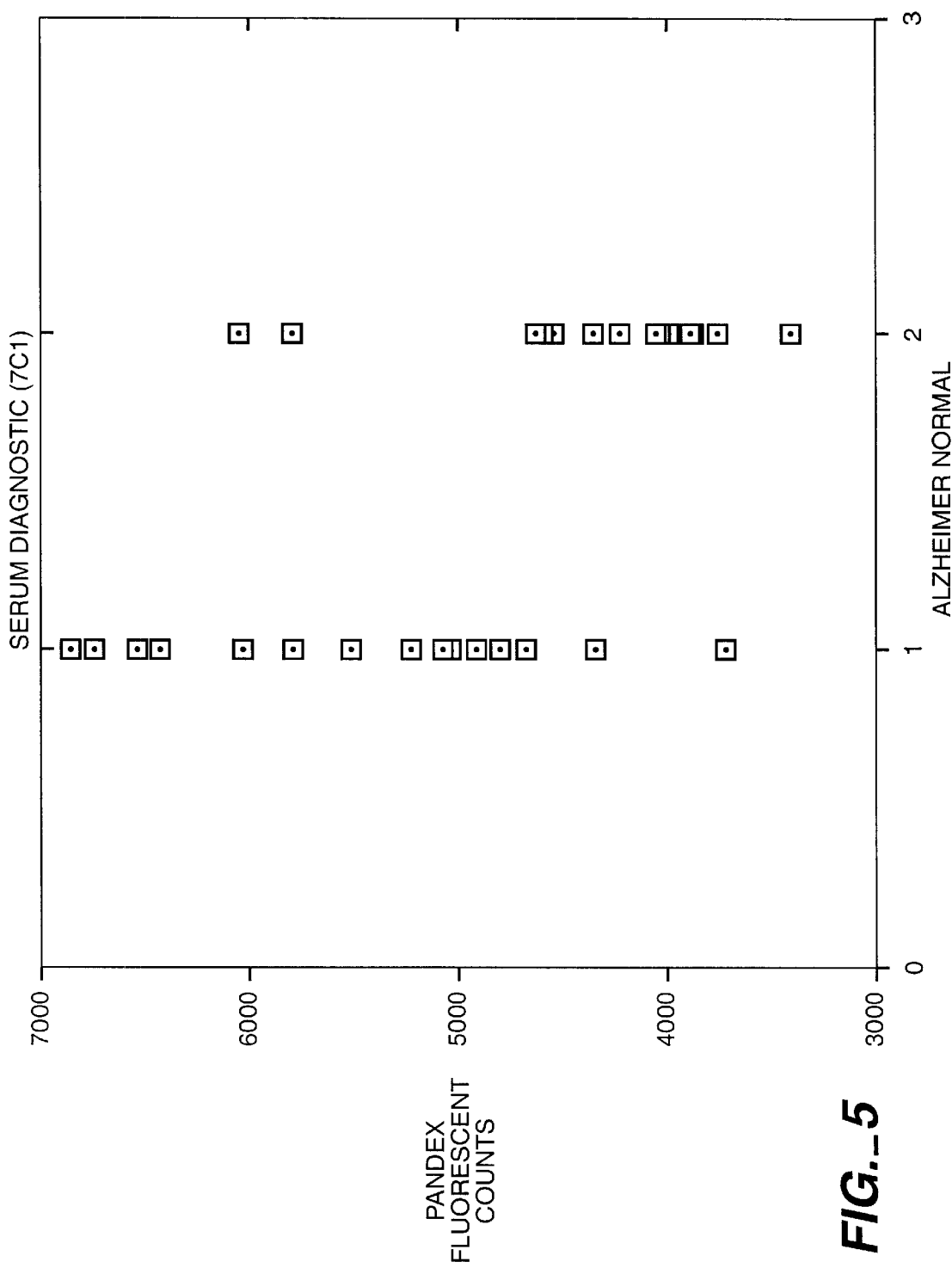
FIG._5

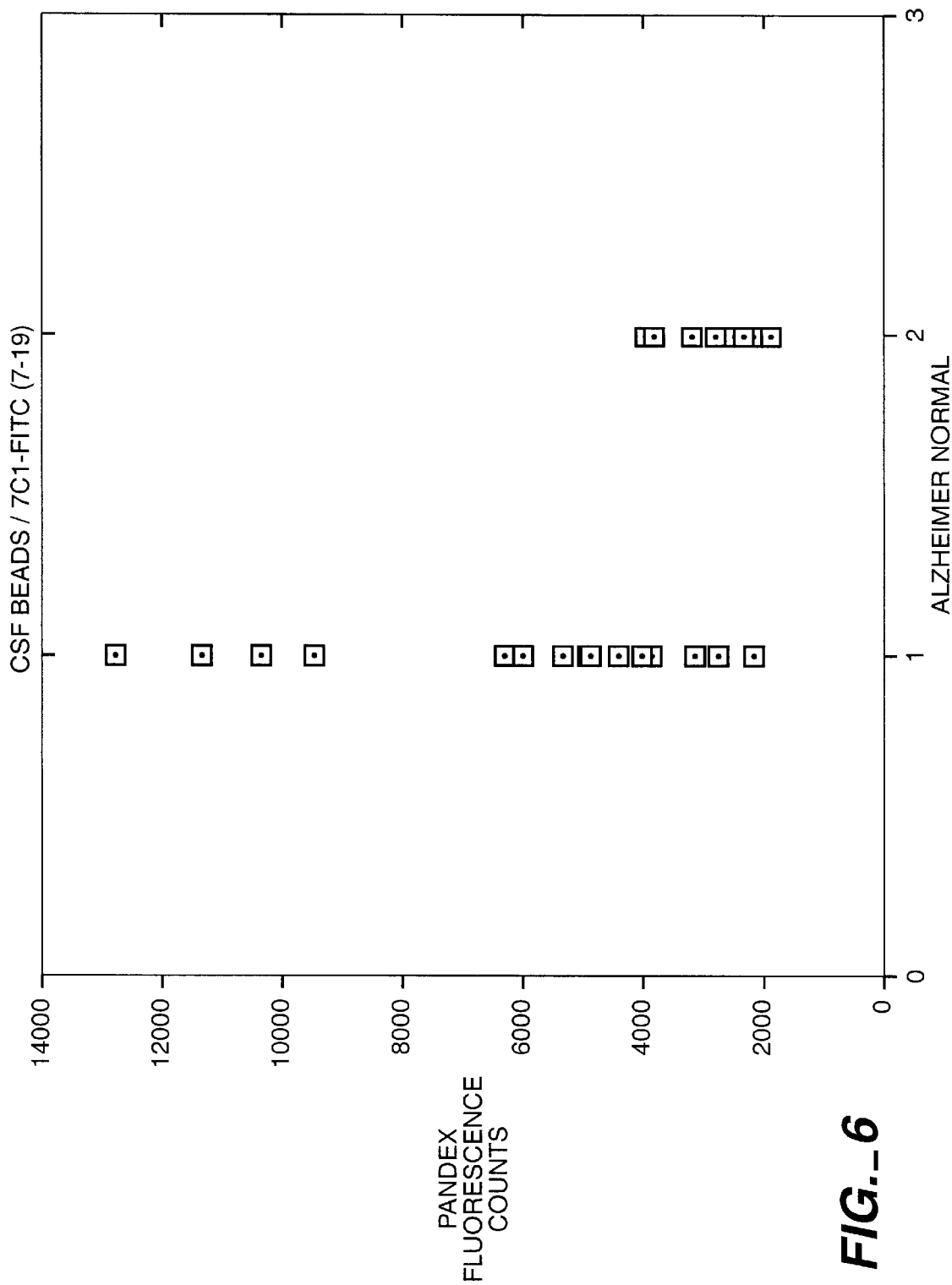
FIG._6

DIAGNOSTIC METHODS FOR ALZHEIMER'S DISEASE

This is a continuation of U.S. application Ser. No. 07/235,055, filed Aug. 19, 1988, abandoned.

BACKGROUND OF THE INVENTION

A. General Diagnosis of Diseases

In most cases, diagnosis of a given disease requires a number of agreed-upon concurrent observations made by the attending physician. For some diseases, such as diabetes, a nearly definitive test, such as a glucose tolerance test, is sufficient to make a correct diagnosis. Most diseases, however, such as atherosclerosis, schizophrenia or lupus erytheomatosus require a number of sophisticated tests to arrive at a probable diagnosis. An extreme example is Alzheimer's disease which is currently only confirmed at the time of autopsy by examination of brain tissue.

The reason for the general scarcity of definitive diagnostic tests—particularly those utilizing biological fluids, such as serum plasma, cerebral spinal fluid or urine—is that diagnostic tests are generally found serendipitously. There currently exists no systematic way of arriving at a novel biological fluid-based diagnostic for a given disease.

This problem is very weighty for diseases of unknown etiology, such as Alzheimer's disease. Numerous other diseases with similar diagnostic problems include multiple sclerosis, amyotrophic lateral sclerosis and lupus erytheomatosus.

From a diagnostic standpoint, Alzheimer's disease represents a great challenge for two reasons. First, the disease affects one out of six individuals over the age of 65 or approximately two to five million individuals in the United States alone; and second, virtually nothing is known about distinguishing characteristics of the plasma or other biological fluids of Alzheimer's patients—current knowledge is limited to distinguishing characteristics of the brain tissue itself.

Several specific distinguishing characteristics have been found within the parenchyma of the brain in Alzheimer's disease. One key feature is the presence of amyloid plaques. These can be of neuritic or cerebral vascular origin. The cerebral vascular amyloid is comprised of a small peptide that is 39 to 42 amino acids in length. Molecular cloning studies have shown that this peptide is most likely a product of a larger precursor whose gene maps to chromosome 21 but ultimately does not necessarily segregate with the familial form of Alzheimer's disease. Therefore, this gene does not constitute the locus for the disease, although such was an attractive hypothesis since trisomy 21 or Down's syndrome patients ultimately portray Alzheimer-like pathology. Another surprising observation is that the amyloid precursor is fairly ubiquitous throughout various organs in the body. This suggests that this protein might be difficult to exploit as a diagnostic tool since its level of expression is already very high in normal healthy individuals.

Attempts have been made to produce monoclonal antibodies to specific brain alterations in Alzheimer's disease and then to utilize these for diagnostic potential. One such antibody, "Alz50," produced by P. Davies using Alzheimer brain as the antigen, does appear to specifically stain neurofibrillary tangles as seen in Alzheimer's, Picks, and Guam-Parkinson diseased brains. There are some data to suggest that this antibody detects an Alzheimer-specific antigen in Alzheimer cerebral spinal fluid that is 68 kdal in mass compared to 60 kdal in normal cerebral spinal fluid. The reproducibility and usefulness of this observation as a diagnostic for Alzheimer's disease has not yet been confirmed by other laboratories.

Another area of potential diagnostic value for Alzheimer's disease in cerebral spinal fluid is the detection of altered forms of tau and ubiquitin proteins. Both of these proteins are thought to be associated with neurofibrillary tangles. Recently, an abstract describing an enzyme-linked assay against paired helical filaments demonstrated a statistical qualitative difference in the signal generated by Alzheimer cerebral spinal fluid, although the overlap between the two sample groups was large.

Prior to this invention, no distinguishing characteristics have been discovered in the plasma or other biological fluids of Alzheimer patients. Prior efforts to look for Alzheimer specific fragments of the amyloid precursor have thus far produced no concrete discriminating data.

B. Haptoglobin Function

Haptoglobin is a member of the chymotrypsinogen serine protease family. It has, however, lost its protease activity due to the histidine lysine-57 and serine alanine-195 substitutions. Its $\alpha_2\beta_2$ structural composition closely resembles that of Factor XI.

Haptoglobin has the unique capacity to bind hemoglobin almost irreversibly. Hence, its function in hemolyzed plasma is to conserve hemoglobin in plasma from destruction in the kidney. Haptoglobin-hemoglobin complexes are specifically readsorbed by the liver where the hemoglobin is recycled.

Currently, the only established use of haptoglobin as a diagnostic marker is in the diagnosis of anemia. Haptoglobin levels often fall dramatically in the anemic state. Its usefulness for this purpose is, however, questionable, since high haptoglobin levels can also occur in an anemic state as well.

Haptoglobin is also a member of a class of proteins termed "acute phase reactants." These proteins are synthesized and released by the liver in response to several types of physiological stress. The hormonal signals involved in the signalling process are thought to include interleukin I and hepatic stimulating factors I and II. Inflammatory processes known to increase levels of acute-phase reactants include arthritis and coronary artery disease.

There are several reports in the literature where an attempt was made to correlate senile dementia of the Alzheimer type with the haptoglobin-1 (Hp-1) allele frequency. The data conflict, however, and the general scientific conclusion is that no such correlation exists.

C. Filamentous Proteins and Alzheimer's Disease

There are two established hallmark brain lesions of Alzheimer's disease: amyloid plaques and neurofibrillary tangles. Amyloid plaques are now known to contain a small peptide termed $A_4$. This peptide has been sequenced and based on that sequence a cDNA clone was isolated containing a much larger precursor that contained within it the sequence of the $A_4$ peptide. Great effort is currently focussed on understanding the role of this precursor protein in the etiology of the disease.

The second hallmark of Alzheimer disease, namely neurofibrillary tangles has proven less amenable to isolation and characterization. The tangles are known to contain at their core paired helical filaments (PHF). These consist of two filaments that twist about each other in an $\alpha$-helix. Methods have been developed to partially purify paired helical filaments as intact structures and although this has increased our understanding of their structure, it has not been possible to solubilize and sequence the principal core protein(s) See, for example, Iqbal, K., et al., *Acta Neurophilogica*, 62:167–177 (1984) which is incorporated herein by reference. Since PHF might contain proteins that are present in plasma or CSF as well as the brain, this material was used in the present invention as an immunogen. In fact, the antibody 7-C1 is described that has usefulness as an Alzheimer's diagnostic. It appears to recognize an intermediate-filament associated protein which is consistent with the PHF immunogen used to raise it.

SUMMARY OF THE INVENTION

Several objects are attendant to this invention.

For example, a first object of the invention is to provide a method for identifying key diagnostic antigens of, or antibodies to, a disease state. This is particularly important in disease states of unknown etiology, such as Alzheimer's Disease.

Another object of the invention is to provide a method for diagnosing a disease state, wherein a key diagnostic antibody is provided, and wherein said key diagnostic antibody was discovered in accordance with the instant invention.

Yet another object of the invention is to provide a method of diagnosing Alzheimer's Disease, using a key diagnostic antibody identified in accordance with this invention.

Still another aspect of the invention is to provide a kit for diagnosing Alzheimer's Disease, including a key diagnostic antibody and means for evaluating the degree of binding of the antibody in a biological sample, as compared to a standard.

A still further object of the invention is to provide key diagnostic antibodies that are effective in the diagnosis of Alzheimer's Disease.

These objects of the invention are realized in the various aspects of the invention set forth below.

A first aspect of the invention is directed to a method for identifying key diagnostic antigens of, or antibodies to, a disease state. According to a first step of this method, an assortment of hybridomas is provided, capable of producing monoclonal antibodies. These hybridomas are prepared from lymphocytes of a host immunized with biological material from a human or animal having the disease state, and myeloma cells. In a second step of this method, a first series of solid supports is coated with a biological sample obtained from at least one subject having the disease state. In a third step, a second series of solid supports is coated with a like biological sample obtained from at least one subject not having the disease state. Finally, the assortment of hybridomas is screened. The screening is accomplished by, first, sequentially selecting individual hybridomas; then, applying each of these selected individual hybridomas to one of each of the first and second series of solid supports; then detecting the degree to which the monoclonal antibodies produced by the individual hybridomas bind to antigens in the samples on the respective solid supports; and finally, comparing, for each selected individual hybridoma, the degree of antibody binding to antigen on the solid support of the first series to the degree of antibody binding to antigen on the solid support of the second series.

A second aspect of the invention is directed to a method for diagnosing a disease state. In a first step of this method, a key diagnostic antibody is provided, which key diagnostic antibody was identified in accordance with the method described above. Then, a biological sample is obtained from the patient in need of diagnosis. The biological sample is contacted with the key diagnostic antibody, and the presence of key diagnostic antibody bound to antigen in the biological sample is detected.

A third aspect of the invention is directed to a method for diagnosing Alzheimer's Disease. In the first step of this method, a monoclonal antibody to a key antigenic site is provided. Then, a biological sample is obtained from a patient in need of or desiring a diagnosis. The biological sample obtained from said patient is then contacted with the monoclonal antibody under conditions that would permit the antibody to bind to a complementary antigen in the biological sample, if such antigen were present therein. Finally, the presence or absence of said bound antibody is detected.

A fourth aspect of the invention is directed to a kit for diagnosing Alzheimer's Disease. The kit comprises a monoclonal antibody capable of binding to a key antigenic site present in a biological sample obtained from a human subject having Alzheimer's Disease, and a means for evaluating the degree of binding of the monoclonal antibody to antigens in a biological sample by comparing it to a standard.

A fifth aspect of the invention is directed to a monoclonal antibody that binds in a greater degree to an acute phase reactant in a biological sample from a patient having Alzheimer's Disease, than to a like acute phase reactant in a biological sample from a patient not having Alzheimer's Disease.

BRIEF DESCRIPTION OF THE DRAWINGS

FIG. 1 is a diagram of the serum-based monoclonal antibody screen.

FIG. 2 is a diagram of the CSF-based monoclonal antibody screen.

FIG. 3 is a bar graph obtained in accordance with the procedure of Example 1.

FIGS. 4, 5 and 6 are scatter graphs obtained in accordance with the procedure described in Example 2.

These Figures will be best understood when reviewed in conjunction with the Detailed Description and Examples set forth below.

DETAILED DESCRIPTION OF PREFERRED EMBODIMENTS

The present invention relates to methods for identifying key differences in biological fluids between healthy and diseased subjects. One such difference discovered by the instant inventors is a difference in the behavior of the a chains of haptoglobin in Alzheimer patients. The instant inventors have discovered biological fluid differences in Alzheimer's patients relating specifically to haptoglobin: approximately 10,000 monoclonal antibodies against Alzheimer plasma were screened, of which only three demonstrated a statistical difference between the levels in 45 Alzheimer patients compared to 45 age-matched controls; all three antibodies were against an epitope on $\alpha$-chains chains of haptoglobin. These antibodies were each generated from different experiments employing different plasma pools for both immunizations and screens. Interestingly, while total haptoglobin levels are not necessarily of diagnostic value, measurement of this epitope of $\alpha$-chain haptoglobin is of diagnostic value, particularly when carried out by the solid-phase methods described herein.

A. Definitions

For the purposes of the instant invention, the following terms are to be understood as having the definitions set forth below.

"Acute phase reactants" are proteins produced in greater quantities in biological fluids, typically in the liver, of patients undergoing acute phase reaction, i.e., a biological stress state induced by trauma such as inflammation, surgery, infection, arthritis, coronary artery disease and the like. Acute phase reactants include, but are not limited to, $\alpha$-chain haptoglobin, $\alpha$-1-antichymotrypsin, C-reactive protein, inter-$\alpha_1$-trypsin inhibitor and proteins involved in the classical and alternate complement pathways including properdin P or factor P.

"Biological material" for immunization of a human or animal is any bodily sample useful for raising antibodies of a host, such as, but not limited to, plasma, serum, whole blood, paired helical fragments, microtubule associated tau, cerebral spinal fluid (CSF), amyloid plaques, urine, any human tissue (such as, but not limited to, brain tissue) and the like. Preferred biological materials are generally serum, plasma or whole blood. Most preferred biological materials are plasma for most immunization applications, and plasma or paired helical fragments for Alzheimer immunizations.

A "biological sample" for screening for antibodies or testing for the disease state is any biological fluid such as whole blood, plasma, serum, urine or CSF. Preferred biological samples are plasma, CSF, serum and urine. Most preferred are plasma and CSF. Preferably the same type of biological fluid used for screening is used for testing, but the biological fluid need not be the same for both applications, and need not be the same as the biological material used for immunization.

A "complementary binding pair" consists of two members—generally, an antibody and an antigen—that tend to bind to one another under physiological conditions. Smaller binding portions of antigens and antibodies (e.g., haptens and the like) can also be considered as complementary binding members of a specific binding pair.

"Greater degree of binding" of a monoclonal antibody for a protein or other antigen of interest in a biological sample obtained from a patient having Alzheimer's disease than for a like protein or antigen in a patient not having Alzheimer's disease, means that a statistically significantly larger quantitative signal will be obtained as a result of antibody-antigen interaction for a sample of a given size from an Alzheimer's patient than in a sample from a patient not having Alzheimer's disease. For example, a key diagnostic monoclonal antibody identified in accordance with this invention has a greater binding capacity for haptoglobin in a patient having Alzheimer's disease than in a healthy person, as determined by the relative intensity of the signal produced when a labelled (second) antibody is used to detect the presence of the key diagnostic antibody bound to haptoglobin in biological samples (coated on a solid support) from diseased versus healthy patients.

A "key diagnostic antibody" is a monoclonal antibody that will bind in greater quantity to a biological sample from a patient having the disease state of interest than to a like sample from a healthy subject. A "key diagnostic antigen" or a "key antigenic site" is the protein or locus on the protein, respectively, to which the key diagnostic antibody binds.

"Immunoaffinity purification" is a method for purifying an antigen. This method typically comprises: covalently binding the complementary monoclonal antibody to a solid phase (typically, a column matrix); running a biological sample such as plasma, the antigen to be purified, over the solid phase (e.g., through the column) to obtain non-covalent binding between the complementary antibody and antigen; and disrupting the antigen-antibody binding to obtain the antigen of interest (e.g., eluting the antigen of interest off the column).

A "matrix" is any cytoskeletal material such as microfilaments, intermediate filaments, microtubules, paired helical filaments or insoluble plaques.

"Polyclonal antisera" for pre-coating a solid support would be antiserum generated preferably in a species other than mouse (i.e., in a species other than that of the host from which the hybridomas were prepared), typically generated against Alzheimer or other disease-specific antigens. Examples are anti-Alzheimer cerebral spinal fluid, anti-paired helical filaments, anti-amyloid plaques and anti-Alzheimer plasma.

A "solid support," for the purposes of this invention, provides a contiguous (substantially uninterrupted) surface for a biological sample to adhere to, such as a spherical surface or the surface of any type of bead-like support, and is typically a particulate support, such as polystyrene beads. A solid support can be pre-treated with polyclonal antisera directed to a subset of proteins of interest, or can be treated with any matrix, such as filamentous proteins, that tends to immobilize the antigen or antigens of interest. Such a pre-treated solid support is contemplated to be within the meaning of "solid support" for the purposes of this invention, as is a solid support that has not been pre-treated.

B. General Method for Identifying Key Diagnostic Antibodies and/or Antigens in a Disease State The general method for identifying key diagnostic antigens and/or antibodies is set forth in the Summary of the Invention. However, a description of preferred methods follow.

In general, a most preferred method for identifying key diagnostic antigens or key diagnostic antibodies, useful for diagnosing a disease state, comprises performing substantially the following steps, or equivalents thereto. First, a nonhuman, mammalian host is immunized with normal human biological material, such that the host becomes substantially incapable of producing antibodies to such material. (Where a biological sample, not present in healthy humans, such as, e.g., paired helical fragments, is used for production of hybridomas, this tolerization step is omitted.) Then, the host is immunized with like biological material from at least one human patient diagnosed as having the disease state. Then, lymphocytes from the host are fused with myeloma cells to produce an assortment of hybridomas capable of producing monoclonal antibodies. Individual hybridomas are screened from the assortment by applying them separately to a first solid support coated with a biological sample from at least one patient diagnosed as having the disease state and to a second solid support coated with a biological sample from at least one patient not having the disease state. For each hybridoma, the degree to which the antibodies produced by the hybridoma bind to the antigens on the respective first and second solid supports is first detected and then compared. Individual hybridomas producing the greatest relative difference in degree of monoclonal antibody binding are selected for re-screening. In the re-screening process, the selected hybridomas are applied individually to a first and second pluralities of additional solid supports, where each support in the first plurality is coated with a biological sample obtained from a different individual diagnosed as having the disease state, and each support in the second plurality is obtained from a different individual diagnosed as not having the disease state. Finally, for each re-screened hybridoma, the relative degree of binding of monoclonal antibodies produced by the hybridoma to the respective first and second pluralities of additional solid supports is evaluated. The antibodies produced by the hybridomas showing the greatest difference in binding to the respective control and disease coated supports are preferred key diagnostic antibodies. It will be apparent to one of ordinary skill in the art that some steps described in this paragraph are optional and are set forth for the purpose of illustrating the most preferred embodiments, but are not required for practicing the invention in its broadest aspects.

Additional details directed to the currently preferred methodology for identifying monoclonal antibodies or antigens of diagnostic value in testing plasma, or any biological sample of choice, follow here and in the Examples.

After defining the disease to which a diagnostic is to be made, a biological sample or macromolecule characteristic of the disease, preferably serum, plasma, cerebral spinal fluid (CSF), or paired helical fragments (PHF) is obtained from a well-characterized pool of patients with the disease. This pool might be from as few as one patient, or as many as 100 patients, but is preferably from at least two patients and most typically would be about 5 to about 15, and most preferably about 10, samples mixed equally.

Another numerically matched, normal pool of like biological sample, e.g., plasma, is obtained from a random group of age-matched individuals, some of whom might be suffering from unrelated diseases—particularly those diseases from which the diagnostic assay is meant to differentiate—but who are clearly not suffering from the disease for which the diagnostic is to be made.

The normal plasma pool is then used to tolerize mice. This procedure reduces or abates the ability of the mouse in young adulthood to mount an immune response against the antigens to which it was tolerized. The mice are then immunized with the pooled plasma from the patients with the disease. Thus, the "disease-specific" antigens are recognized by the tolerized mice. Following immunization, the mice are then prepared to produce hybridomas using standard procedures with the Sp2/0 myeloma cell fusion partner.

An important aspect of the invention is the method of screening the various hybridomas produced from the tolerized and immunized mice. One way of performing this task is to coat polystyrene surfaces, preferably sub-micron size particles such as Pandex polystyrene 0.83 micron beads, with both pools of plasma or CSF or other biological material—i.e., the pool from normal and the pool from the disease samples.

The hybridomas obtained from the fusion above are then incubated with the plasma or CSF coated particles for at least about 4 minutes, typically about 5 to about 30 minutes (although it can be left overnight), and preferably about 10 to about 15 minutes, and the particles are then washed. Hybridomas that bind to the particles are detected by the use of a second antibody against mouse IgG and IgM, to which a label is attached. The label for detection can be an enzyme, a radioactive isotope or a fluorophore. Typically, fluorescein-labeled goat-anti-mouse IgG is used.

Following another wash step, the label is quantitated by usual methods. This generally involves calorimetric, gamma or fluorescent quantitation. Preferably, the latter method is performed.

Those hybridomas that give a higher signal on the diseased CSF or plasma are then chosen for further analysis. The secondary analysis typically involves analyzing a modest number of disease CSF or plasma samples compared to control fluid samples. Preferably, approximately 15 diseased samples and 15 control samples are used. Those hybridomas that continue to demonstrate diagnostic value, as determined by a demonstrated statistical difference in signal levels of control and diseased fluids, are then tested on a larger patient population (typically, 45 diseased samples and 45 control samples). Monoclonal antibodies that pass at least the first screening, and preferably the second and third screenings, are useful as diagnostics, and are referred to as "key diagnostic antibodies" herein.

This method for identifying key diagnostic antibodies or antigens is preferably carried out as set forth in Example 1, for Alzheimer's Disease. Of course, one skilled in the art will appreciate that the details of the method can be varied, and the method can easily be adapted for identifying key diagnostic antibodies or antigens for other disease states.

C. Diagnosis of a Disease State

Once the key diagnostic antibody is identified for the disease state of interest, diagnosis of the disease state can be accomplished generally by obtaining a biological sample from a patient in need of diagnosis, contacting the sample with the key diagnostic antibody, and detecting the presence or quantity of the complementary binding pair of interest, i.e., the key diagnostic antibody bound to antigen in the sample. The complementary binding pair can be detected, for example, by using a key diagnostic antibody labelled with a fluorophore, a radioactive isotope, or a member of a calorimetric signal-producing enzyme or substrate pair. The resulting signal can be quantitated, for example, by comparison with a standard curve, generated as described in Example III. The diagnostic assay can be carried out as a competitive assay, as described in Example III, where the haptoglobin (or other key diagnostic antigen) in the sample competes for labelled key monoclonal antibody binding with the haptoglobin (or other antigen) pre-coated onto the beads; or the assay can be carried out as a sandwich assay, e.g., as described in Example IV, where key monoclonal antibody binds with its complementary binding member in the sample of the patient, and then a labelled polyclonal (or monoclonal) antibody, which is also a complementary binding member to the key diagnostic antibody, is added to detect the key monoclonal antibody bound to key antigenic site in the sample.

In still another variation, CSF or plasma samples may be coated directly on to the solid phase and the labeled key diagnostic antibody is then allowed to bind to the key diagnostic antigen. The amount of binding is then measured either enzymatically fluorometrically, colorimetrically or by radioactivity.

Other assay methods that utilize the key diagnostic antibodies identified in accordance with this invention will be apparent to one of ordinary skill in the art.

D. Diagnostic Kit

A diagnostic kit according to this invention comprises at least a key diagnostic monoclonal antibody. Depending on the configuration, a solid phase will be supplied together with the labeled or unlabeled key diagnostic antibody. In some cases, polyclonal antisera against the key diagnostic antigen will also be supplied to assist in detecting the key diagnostic antigen. Optionally, a series of solutions having a number of different concentrations of an antigen will also be included in the kit, for developing a standard curve.

In one embodiment, a competitive immunoassay is provided wherein the antigen is labeled fluorescently, radioactively or with enzyme. The key diagnostic monoclonal antibody is attached to the solid phase and incubated with labeled key diagnostic antigen. A standard curve is generated by the addition of unlabeled antigen. The concentration of the key diagnostic antigen in a sample of biological fluid is then determined by the ability of that fluid to compete for the binding reaction with reference to the standard curve.

In another similar competitive assay format, the key diagnostic antigen is attached to the solid phase and the labeled key diagnostic antibody is added. Various concentrations of the unlabeled antigen are incubated with the labeled antibody to form a standard curve. In the same manner as above, a biological fluid is tested by its ability to compete for the binding reaction: the antigen in the biological sample competes with the antigen bound to the solid phase for binding to the antibody in solution.

In another embodiment, an immunoassay is provided where the biological fluid is permitted to bind directly to the solid phase. The labelled key diagnostic antibody is then added to generate a signal, which is compared with a set of known standards.

In still another embodiment, polyclonal antisera against the key diagnostic antigen are attached to the solid phase and incubated with the biological sample (or key diagnostic antigen, for the purpose of making a standard curve). Then a labeled key diagnostic antibody is added to generate a signal.

In yet another embodiment, an immunoassay is provided where the key diagnostic antibody is attached to the solid phase and incubated together with the key diagnostic antigen (or biological fluid to be quantitated). Labeled polyclonal antisera specific to the antigen are then added to generate a signal. The concentration of the antigen in the biological fluid is based on its ability to produce a signal in the assay relative to a standard antigen of known concentration.

Other embodiments of the diagnostic kit of this invention will be apparent to one of ordinary skill in the art.

E. Monoclonal Antibodies

Monoclonal antibodies useful for the diagnosis of Alzheimer's Disease were obtained in accordance with the methodology described in section IV A above and Example I below. The corresponding hybridoma cells, specifically 3H6, 5D8 and 3H11 for plasma and 7-C1 for CSF, were subcloned and vials frozen for future reference. These are on deposit with the ATCC and have respective accession numbers of HB9789 (for cell line 3H6), HB9790 (for cell line 5D8), and HB9791 (for cell line 7-C1).

EXAMPLES

It should be understood that the foregoing general description and the following examples are illustrative of preferred embodiments, and are not intended to limit the scope of the invention. The invention is to be defined by the appended claims, and all equivalents thereto.

Example I: Protocols For Monoclonal Antibody Production and Selection (5D8, 3H6 and 3H11 Antibodies)

A. Tolerization Protocol

The following protocol was used to tolerize the mice used for the 5D8 antibody, and similar protocols were used for antibodies 3H6 and 3H11. Pregnant mice were purchased from Simonsen Labs (Gilroy, California). They arrived seven days before delivery to subject the mothers to a minimum of stress. The mice were checked twice daily to help minimize the time between birth of the pups, and the first injection. All mothers delivered by 7 a.m. on day 7.

The injections began immediately after neonates were discovered. Mothers were removed from the cage. Neonates were handled in a flow hood using sterile instruments.

Neonates were injected on days 0, 2, 4, 6, 8, and 10. Each injection consisted of 25 $\mu$l containing 1 mg of pooled normal serum. All neonates were injected intraperitoneally. After the last injection, neonates were left undisturbed until day 21.

Neonates were weaned from their mothers on day 21. Injection of the desired immunogen also began this day. The initial injection was 50 $\mu$g of pooled Alzheimer serum emulsified in Complete Freunds Adjuvant (CFA). Subsequent injections were done the third and sixth day after the initial injection. These injections also contained 50 $\mu$g; however, the serum was emulsified in Incomplete Freunds Adjuvant. The injections were all intraperitoneal.

Serum from these mice was assayed for response on both normal and Alzheimer serum. The two mice with the best titer were chosen for fusion. These mice were injected intravenously with 50 $\mu$g of Alzheimer serum, as well as intraperitoneally with 50 $\mu$g of Alzheimer serum. The fusion was done three days after this injection.

B. Immunization Protocol

The injection schedule used to generate antibody 7C1 was as follows. Approximately 10 $\mu$g/ml of paired helical filaments (PHF) were emulsified in Complete Freunds Adjuvant, and injected intraperitoneally. On day 15, and day 28 post initial injection, approximately 5 $\mu$g of PHF was emulsified in Incomplete Freunds Adjuvant was injected intraperitoneally. The mouse was rested for 21 days, and then injected with approximately 10 $\mu$g of PHF, intraperitoneally. The mouse was fused three days later. There were no changes in the fusion protocol.

Antibody 3H6 was produced using the following immunosuppression protocol. 200 $\mu$g of pooled normal human serum was injected into the mouse in conjunction with 100 mg/kg of body weight of cyclophosphamide. The mouse was injected with cyclophosphamide only, 24 hours and 48 hours after the initial injection. This series of injections was repeated fourteen days later. These injections were all intraperitoneal.

The mouse rested without injection for three months. The mouse was then injected with 200 $\mu$g of pooled Alzheimer serum intravenously. The mouse was fused three days later. The only change from standard fusion protocol was that the number of SP2/0 cells used was $7.5 \times 10^7$.

C. Fusion Protocol

The fusion protocol used required the following materials: Dulbecco's Modified Eagle Media, (DMEM) with high glucose; Polyethylene Glycol 1500, screened for fusions, obtained from Boehringer Mannheim, West Germany; Fetal Bovine Serum (FBS), obtained from JR Scientific, Woodland, Calif.; 200 mM tissue culture grade Glutamine; $10^{-2}$M tissue culture grade hypoxanthine; 200 mg/ml of tissue culture grade Azaserine; 0.93 percent ammonium chloride; 3% Dextran, the high molecular weight fraction; 1M tissue culture grade HEPES Buffer, pH 7.2; a 35 ml sterile petri dish; sterile forceps and dissecting scissors; fifteen sterile 96-well flat bottom tissue culture plates with lids; a twelve channel pipet and sterile tips therefor; two sterile microscope slides with frosted ends; SP2/0 cells obtained from American Type Culture Collection (Rockville, Md.).

On the day of the fusion two different media were prepared. The first was a growth medium containing 400 ml of DMEM, 100 ml of FBS, 5 ml of 200 mM glutamine, 7.5 ml of 1M HEPES buffer, pH 7.2, and 5 ml of $10^{-2}$M hypoxanthine. The other medium that was prepared was the selection media, comprising 75 ml of growth media to which was added 750 $\mu$l of 200 $\mu$g/ml azaserine.

The mouse was sacrificed and then immersed in 70% ethanol for 10 seconds. The mouse was placed in a flow hood, and the spleen was aseptically removed, and placed in a 35 mm petri dish containing 5 ml of growth media. The spleen was dissociated between the frosted ends of the slide. The spleen cell suspension was placed in a 15 ml sterile tube. The petri dish was rinsed with 10 ml of growth media and the cell containing washings placed in the same 15 ml tube.

The SP2/0 cells were counted. (The density was generally greater than about 0.5 million cells per ml, yet, less than about 0.9 million per ml.) The viability of the cells was generally greater than about 95% as estimated by trypan blue exclusion. Approximately fifty million cells were then placed into sterile 50 ml tubes. Both the spleen cells and the SP2/0 cells were then centrifuged in a clinical centrifuge for 10 minutes at 500×g.

The supernatant was removed from the spleen cells, and they were resuspended in 8 ml of ammonium chloride at about 4° C. This was allowed to sit on ice for 5 minutes.

The SP2/0 cells were resuspended in 15 ml of plain DMEM. When the five minutes incubation of the spleen cells was complete, the suspended spleen cells were removed from debris pellet and added to the SP2/0 cells. DMEM was added to this cell mixture until the total volumes is 25 ml. 25 ml of the 3% dextran was added to the spleen, SP2/0 cell mixture and this incubated for 5 minutes. The cells were centrifuged at 500×g for 10 minutes.

The supernatant was removed from the pellet, and the pellet was then loosened by vortexing. 1 ml of the PEG 1500 was added. The tube was then vortexed and slowly rotated for one minute. This step was the actual fusion step.

25 ml of DMEM were added to the tube and this was incubated for one minute. After this incubation, 25 ml of growth media were added and incubated for one minute. The cells were centrifuged at 500×g.

The pellet was resuspended in 75 ml of selection media. A 12 channel pipet was used to place 50 µl into each well of the fifteen 96-well plates.

Two days after the fusion each well was fed 50 µl of growth media. On day five post fusion, 50 µl were removed and the fusion was fed 100 µl of growth media. Visible hybrids were observed between day seven post fusion and day ten post fusion. At this time, the fusion was fed 100 µl of growth media. Screening generally began around day ten. If hybrids were not ready to be screened on day ten, 150 µl of media were removed and 150 µl of fresh growth media were fed thereto.

D. Screening Protocol

Screens for Alzheimer-specific hybridomas were performed by adsorbing pooled plasma diluted at 1.0 mg/ml in 100 mM $NaHPO_4$ (pH 5.5) onto 0.8 µm polystyrene beads (Pandex labs). After a 90 minute incubation at 21° C., the particles were washed 3 times in wash buffer comprising 50 mM $NaHPO_4$ (pH 7.4), 150 mM NaCl and 0.1% bovine serum albumin. The particles could be stored from about 4 to about 6 weeks in this solution plus 0.05% w/v sodium azide, without detectable loss of activity.

For the actual screens, a Screen Machine® (fluorescent reader) manufactured by Pandex Labs was employed. Typically, 20 µl of a 0.25% (w/v) solution of coated particles either coated with control or Alzheimer disease plasma or CSF was added to all wells. 25–50 µl of hybridoma tissue culture supernatant were then added and allowed to incubate for 15 minutes at 21° C. The wells were then automatically aspirated (by vacuum) and washed 3 times with wash buffer. Fluorescein-labeled goat-anti-mouse IgG (5 µg/ml in wash buffer) was then added to all wells (20 µl/well) and incubated for 15 minutes at 21° C. The wells were then aspirated and washed again and finally the level of fluorescence was automatically quantitated. These protocols are schematically, depicted in FIGS. 1 and 2 for the serum and CSF assays, respectively.

Potential diagnostic monoclonal antibodies were first screened on pools of Alzheimer Disease plasma or control plasma made up of 10 samples each. Those that demonstrated a statistical difference in the two pools were then re-screened on 30 individual plasmas made up of 15 Alzheimer Disease plasmas and 15 control plasmas. Those antibodies that continued to show a statistical distinction based on a Wilcon-Mann ranked-order test were rescreened on 45 Alzheimer's Disease and 45 control plasmas and the diagnostic criteria re-assessed. Antibodies 3H6, 5D8, 3H11 and 7-C1 all demonstrated a statistically valid distinction between Alzheimer and control plasmas.

Monoclonal antibodies that demonstrated a differential signal between Alzheimer CSF or plasma were then rescreened. The corresponding hybridoma cells, specifically 3H6, and 5D8 for plasma and 7-C1 for plasma or CSF, were subcloned and vials frozen for future reference. These are on deposit with the ATCC and have respective accession numbers of HB9789 (for cell line 3H6), HB9790 (for cell line 5D8), and HB9791 (for cell line 7-C1).

For antibody 3H6, a consistent 1.6 elevation of immunoreactivity was seen in Alzheimer pooled plasmas relevant to control pools. When 15 Alzheimer disease and control patients were examined again, a large statistical difference was seen ($p<0.05$). Finally, when 50 control and 50 disease samples were examined, the statistical difference remained evident ($p<0.02$).

E. Identification and Results 10 mg of purified 3H6 monoclonal antibody was attached to CnBr-activated Sepharose-4B as described by the manufacturer. 2 mls of pooled Alzheimer plasma were diluted to 50 mls with 50 mM $NaHPO_4$ (pH 7.5), 150 mM NaCl and chromatographed at 0.5 ml/min. The column was then washed with phosphate-buffered saline until $OD_{280}=0.00$. 0.1M glycine (pH 2.8) was then added and a peak of absorbance was eluted. This material was subjected to analysis by gas-phase N-terminal sequence analysis and two sequences emerged. One was the α-chain of haptoglobin and the other was the β-chain. This finding was consistent with the molecular weights of the proteins identified by both Western blot analyses and SDS-PAGE analysis of the immunoaffinity-purified material.

SDS-PAGE and immunoblot analysis was used to identify the antigens detected by the 3H6 monoclonal antibody in control and Alzheimer patient plasmas. Sodium-dodecyl sulfate polyacrylamide gel electrophoresis of plasma (2 µl/lane) was performed followed by electrophoretic transfer to Immobillon® (transfer paper obtained from Millipore, Bedford, Mass.). The blot was then incubated with 3H6 (0.5 µg/ml) for 2 hours at 21° C. followed by incubation with alkaline phosphatase labelled goat-anti-mouse IgG (2 hours at 21° C.). The 3H6 monoclonal antibody binding was finally visualized by the addition of a colorimetric probe for alkaline phosphatase. The protein stain showed the presence of three major proteins of 40, 25 and 14 kdal, corresponding to the β-chain of haptoglobin, and the $\alpha_2$ and $\alpha_1$ chains of haptoglobin, respectively.

A bar graph is shown in FIG. 3, for the 3H6 monoclonal antibody used on 40 Alzheimer and control samples. There was a general elevation in the levels of antibody immunoreactivity in Alzheimer patients relative to control individuals.

To identify what differences, if any, in haptoglobin, might account for the difference in the 3H6 binding detected by the Screen Machine® (Pandex) analysis, reversed-phase chromatography of normal and Alzheimer plasma was performed followed by analysis for immunoreactivity. The profile of 3H6 immunoreactivity showed that in Alzheimer patients a unique peak of immunoreactivity was eluted at 44–48% acetonitrile. Thus, the measurement of this material in plasma is highly diagnostic for the disease.

Example II (7-C1 Antibody)

Using similar methodologies described in Example 1 above, a monoclonal antibody termed 7-C1 was identified that recognizes an antigen that is elevated in the CSF of Alzheimer's patients (FIG. 4). CSF from 50 individuals showed that Alzheimer patients frequently have an elevation of the 7-C1 antigen. Western blot analysis demonstrated that the antibody recognized an antigen of about 70 kdal in the cerebral spinal fluid of Alzheimer patients. This antigen was also present, in lower levels, in the cerebral spinal fluid of age-matched controls. Analysis of 30 plasma samples showed a similar trend (FIG. 5). 7-C1 immunoaffinity chromatography was performed on 400 mls of plasma from Alzheimer disease patients and control individuals. Protein was eluted from both the control and Alzheimer disease plasma. This material was subjected to HPLC using an acetonitrile 0.1% trifluoroacetic acid system. 7-C1 immunoreactive material from control plasma resolved poorly, aside from minor peaks, and was recovered predominantly in the 80% acetonitrile wash. Equivalent analysis of material from the Alzheimer disease plasma revealed a major peak of protein that eluted at 36% acetonitrile. N-terminal amino acid sequence analysis of this material gave Asp-Pro-Val-Leu-X-Phe-Thr-Gln-Tyr-Glu. This is the precise N-terminus of human Factor P, also known as properdin P, where X=Cys.

Example III: 3H6 Competitive Assay

A competitive assay was used to quantify the levels of 3H6 immunoreactivity in plasma. The monoclonal antibody, 3H6 was purified from ascites fluid by standard ammonium sulfate fractionation followed by DEAE ion exchange chromatography. The purified antibody 1 mg) was covalently labeled with fluorescein isothiocyanate and the conjugated antibody was separated from free fluorescein by G-25 sephadex chromatography. This material constituted the "fluorescent label" in the assay.

The "solid phase" of the assay was generated by incubating purified haptoglobin at 75 $\mu$g/ml with 0.8 $\mu$m polystyrene particles. The standard curve was generated by incubating various concentrations of purified haptoglobin with the fluorescent label and the solid phase. 3H6,immunoreactivity was determined by adding various amounts of plasma rather than standards to the assay mixtures.

Example IV: Indirect 7-C1 Immunoassay

The 7-C1 immunoassay utilized the following components: a) a solid phase consisting of polystyrene beads coated with IgG against human fetal tau, Alzheimer cerebral spinal fluid and ubiquitin; b) a sample containing either CSF or plasma of a given patient; c) 7-C1 media containing approximately 5 $\mu$g /ml antibody; and d) fluorescein isothiocyanate-labeled-second antibody—goat anti-mouse IgM to detect the bound 7-C1 antibody, Components a) and b) were incubated together for approximately 15 minutes at 21° C. followed by two washing taps by centrifugation (12,000 g, 3–5 min.) in phosphate buffered saline containing 0.1% (w/v) bovine serum albumin and 0.05% (w/v) NaN$_3$. Component c) was then added and incubated for 15 minutes at 21° C. followed by an automated wash and the addition of d). After another incubation for 15 minutes at 21° C. there was a final wash and the fluorescence was measured.

The entire assay was performed by a Screen Machine®. The amount of 7-C1 immunoreactivity was proportional to the amount of detected fluorescence (FIGS. 4 and 5).

Example V: Direct 7-C1 Immunoassay

For this methodology, 7-C1 antibody was purified from 10 mls of ascites fluid to near homogeneity by affinity chromatography on a goat-antimouse IgM affinity matrix. One mg of purified 7-C1 was then labeled directly with FITC to a molar ratio of 38 FITC: 1 mole of 7-C1 antibody.

Polystyrene beads were coated with the CSF or plasma to be diagnosed at a dilution of either 1:2 or 1:10 respectively in 0.1M NaHPO$_4$ (pH 5.5) at a bead concentration of 0.25% (v/v). The coated beads were thoroughly washed three times by centrifugation 12,000 g, 5 min) in phosphate-buffered saline containing 0.1% w/v) bovine serum albumin and 0.05% (w/v) NaN$_3$.

To quantitate the amount of 7-C1 immunoreactivity, 20 $\mu$l of the polystyrene beads were incubated with 20 $\mu$l of 10 $\gamma$/ml FITC-7-C1 in 40 $\mu$l total volume for 15 minutes at 21° C. The beads were then washed three times in an automated fashion by the screen machine and fluorescence was measured. Under these conditions, Alzheimer CSF is highly elevated relative to control CSF samples (FIG. 6). Hybridomas 3H6, 5D8, and 7-C1 have been deposited under the terms of the Budapest Treaty with the American Type culture Collection, 10801 University Boulevard, Manassas, Va. 10110, under the accession numbers ATCC HB9789, HB9790, and HB9791, respectively.

What is claimed is:

1. A method for aiding in diagnosing Alzheimer's Disease ("AD") in a subject, comprising the steps of:
    a) contacting a biological fluid from said subject with a monoclonal antibody ("mAb") that binds specifically and to a statistically greater degree to a complementary acute phase reactant antigen in a biological fluid obtained from a subject having AD than to an antigenic site in a biological fluid from a subject not having AD, under conditions such that an antigen-antibody binding complex forms between said mAb and said complementary acute phase reactant antigen present in said fluid, if such an acute phase reactant antigen is present therein;
    b) detecting said binding complex;
    c) correlating the formation of said binding complex with the presence of AD.

2. A method of claim 1, wherein said biological fluid comprises serum, plasma, urine or cerebrospinal fluid.

3. A method of claim 1, wherein said mAb is complementary to acute phase reactant antigen $\alpha$-chain haptoglobin.

4. A method of claim 1, wherein said mAb is complementary to acute phase reactant antigen $\alpha$-1-antichymotrypsin.

5. A method of claim 1, wherein said mAb is complementary to acute phase reactant antigen C-reactive protein.

6. A method of claim 1, wherein said mAb is complementary to acute phase reactant antigen inter-$\alpha$-1 trypsin inhibitor.

7. A method of claim 1, wherein said mAb is complementary to acute phase reactant antigen properdin P.

8. A method of claim 1, wherein said detecting comprises the steps of:
a) attaching a label to said mAb; and
b) detecting said label in said binding complex.

9. A method of claim 8, wherein said label is a fluorescent label.

10. A method of claim 1, wherein said detecting comprises detecting a second labeled antibody that is complementary to said mAb.

11. A method of claim 1, wherein said mAb is the 3H6 mAb.

12. A method of claim 1, wherein said mAb is the 5D8 mAb.

13. A method of claim 1, wherein said mAb is the 7-C1 mAb.

14. A mAb that binds specifically and to a statistically greater degree to a complementary acute phase reactant antigen present in a biological fluid from a subject having AD than to an antigenic site in a biological fluid from a subject not having AD.

15. A mAb that binds specifically and to a statistically greater degree to a complementary α-chain haptoglobin in a biological fluid from a subject having AD than from a subject not having AD.

16. A mAb that binds specifically and to a statistically greater degree to a complementary α-1-antichymotrypsin in a biological fluid from a subject having AD than from a subject not having AD.

17. A mAb that binds specifically and to a statistically greater degree to a complementary C-reactive protein in a biological fluid from a subject having AD than from a subject not having AD.

18. A mAb that binds specifically and to a statistically greater degree to a complementary inter-α-1-trypsin inhibitor in a biological fluid from a subject having AD than from a subject not having AD.

19. A mAb that binds specifically and to a statistically greater degree to a complementary properdin P in a biological fluid from a subject having AD than from a subject not having AD.

20. 3H6 hybridoma (ATCC Accession No. HB9789).

21. The mAb produced by 3H6 hybridoma.

22. 5D8 hybridoma (ATCC Accession No. HB 9790).

23. The mAb produced by 5D8 hybridoma.

24. 7-C1 hybridoma (ATCC Accession No. HB9791).

25. The mAb produced by 7-C1 hybridoma.

26. A kit for aiding in diagnosing AD in a subject, comprising, in separate compartments, a given amount of a mAb complementary to an acute phase reactant antigen that is statistically elevated in a biological fluid from a subject having AD as compared to a subject not having AD, and, optionally, labeled mAbs for detecting binding between said mAb and said complementary acute phase reactant antigen.

27. A kit of claim 26, wherein said mAb is 3H6 mAb.

28. A kit of claim 26, wherein said mAb is 5D8 mAb.

29. A kit of claim 26, wherein said mAb is 7-C1 mAb.

* * * * *